(12) United States Patent
Mazzilli

(10) Patent No.: US 8,765,063 B1
(45) Date of Patent: Jul. 1, 2014

(54) AIR FRESHENER CARTRIDGE WITH MOUNTING

(76) Inventor: Mitchell Mazzilli, Palm City, FL (US)

( * ) Notice: Subject to any disclaimer, the term of this patent is extended or adjusted under 35 U.S.C. 154(b) by 546 days.

(21) Appl. No.: 13/209,105

(22) Filed: Aug. 12, 2011

(51) Int. Cl.
*A61L 9/12* (2006.01)

(52) U.S. Cl.
USPC .................... 422/120; 422/5; 239/53; 239/56

(58) Field of Classification Search
USPC .................. 422/5, 120; 239/53, 56, 57, 60
See application file for complete search history.

(56) References Cited

U.S. PATENT DOCUMENTS

| | | | |
|---|---|---|---|
| 4,523,870 A * | 6/1985 | Spector | 454/157 |
| 5,394,506 A * | 2/1995 | Stein et al. | 392/395 |
| 5,407,642 A | 4/1995 | Lord | |
| 5,422,078 A | 6/1995 | Colon | |
| 5,527,493 A | 6/1996 | McElfresh et al. | |
| 5,735,460 A | 4/1998 | Eisenbraun | |
| 5,899,382 A * | 5/1999 | Hayes et al. | 239/56 |
| D411,002 S | 6/1999 | Farmer | |
| 6,197,263 B1 * | 3/2001 | Blount | 422/125 |

* cited by examiner

*Primary Examiner* — Sean E Conley

(74) *Attorney, Agent, or Firm* — Crossley Patent Law; Micah C. Gunn

(57) ABSTRACT

An air freshener cartridge with mounting that includes a housing with a mounting clip configured to releasably engage with an extant air vent cover to removably secure the air freshener cartridge with mounting thereto, the air cartridge with mounting oriented in a position normal the direction of airflow issuing through said vent.

5 Claims, 4 Drawing Sheets

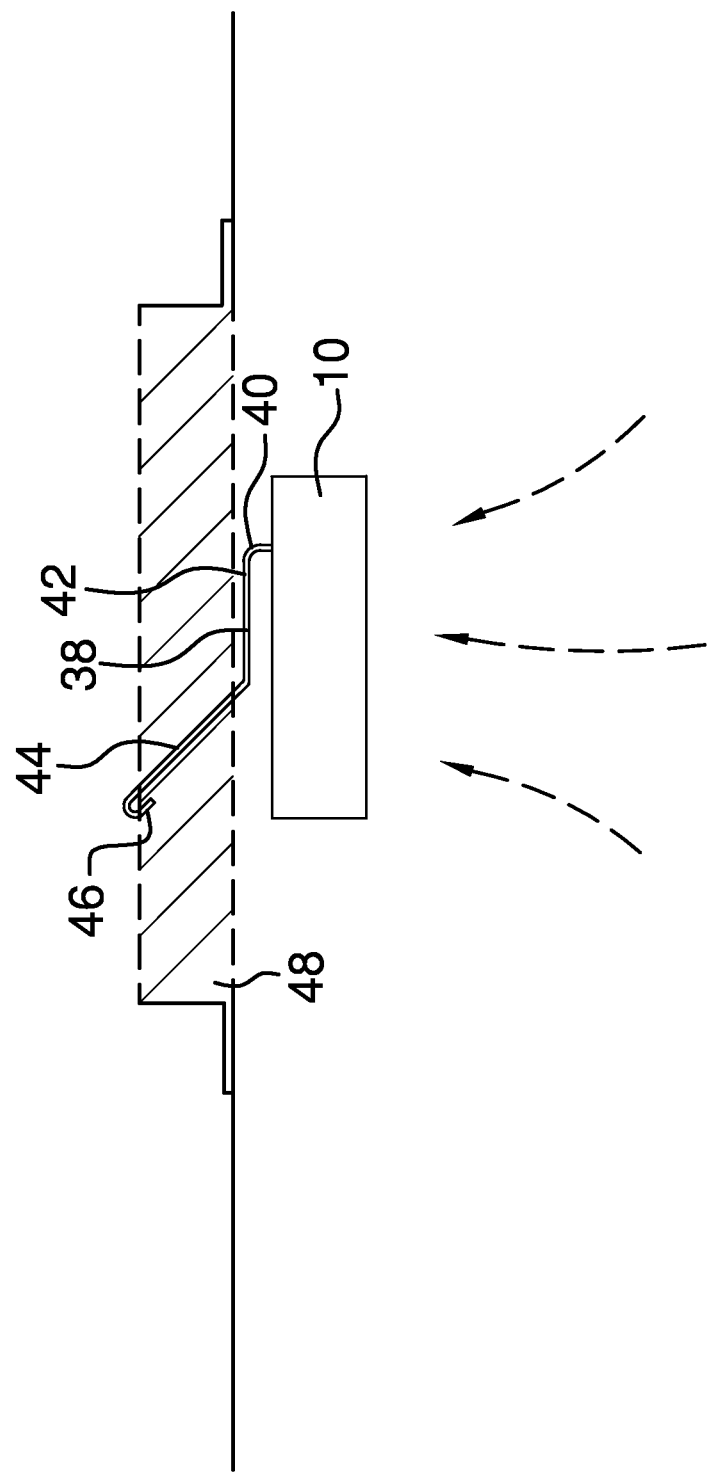

AIR FRESHENER CARTRIDGE WITH MOUNTING

BACKGROUND OF THE INVENTION

Figure 1:
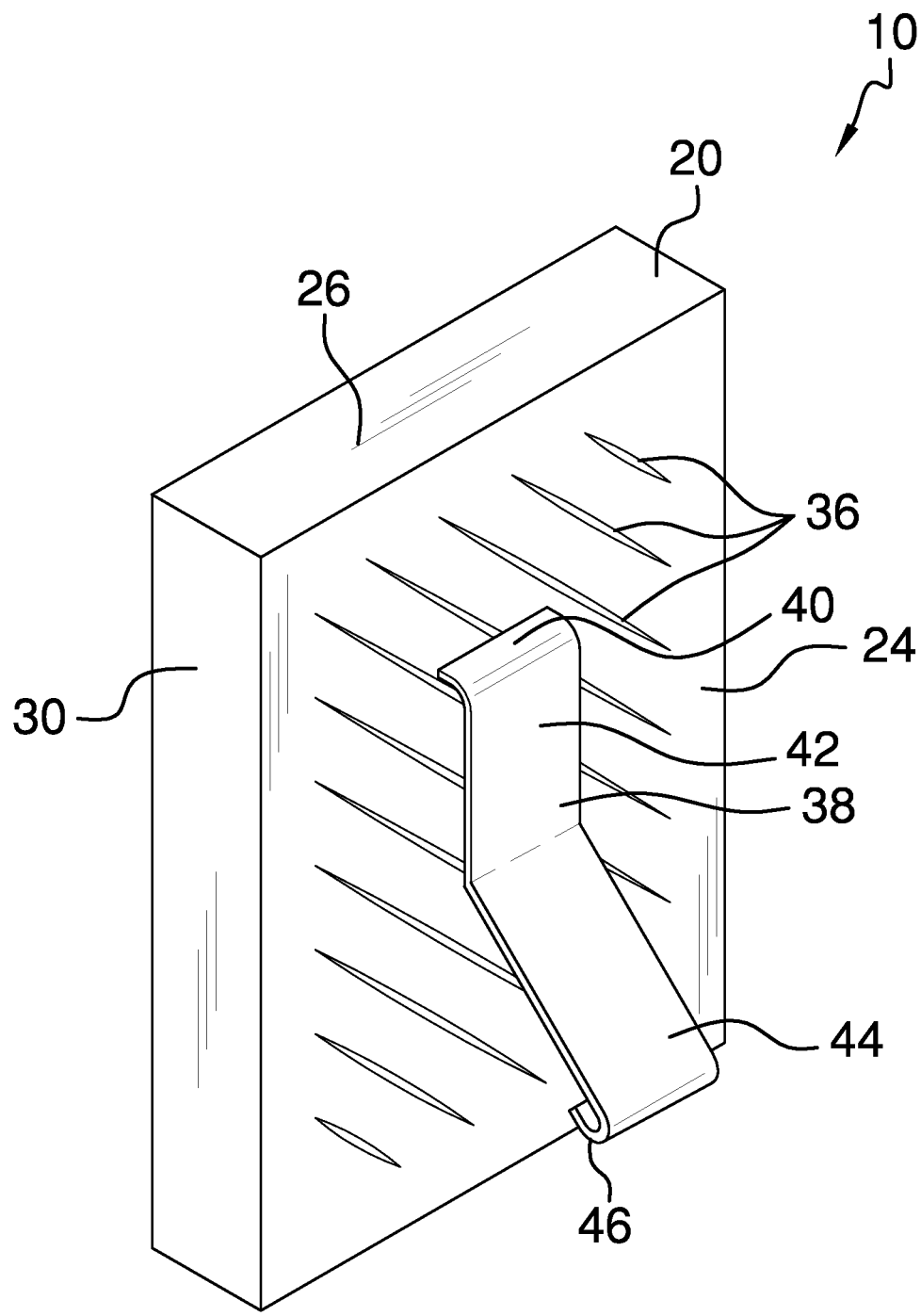

Various types of air freshener cartridge with mountings are known in the prior art. However, what is needed is an air freshener cartridge with mounting that includes a housing with a mounting clip configured to releasably engage with an extant air vent cover to removably secure the air freshener cartridge with mounting thereto, the air cartridge with mounting oriented in a position normal the direction of airflow issuing through said vent.

FIELD OF THE INVENTION

The present invention relates to an air freshener, and more particularly, to an air freshener cartridge with mounting that releasably engages with an extant air vent cover to removably secure the air freshener cartridge with mounting thereto, the air freshener cartridge with mounting oriented in a position normal the direction of airflow issuing through said vent.

SUMMARY OF THE INVENTION

The general purpose of the air freshener cartridge with mounting, described subsequently in greater detail, is to provide an air freshener cartridge with mounting which has many novel features that result in an air freshener cartridge with mounting which is not anticipated, rendered obvious, suggested, or even implied by prior art, either alone or in combination thereof.

Various types of air freshening devices are known in the prior art. But what is needed is an air freshener cartridge with mounting that releasably engages with an extant air vent cover to removably secure the air freshener cartridge with mounting in a position normal relative the direction of airflow issuing through said extant vent. the present device, therefore, has been devised with a mounting clip, which clip releasably engages with an extant air vent cover to removably secure the device thereto, in a position oriented normal the direction of airflow.

The present air freshener cartridge with mounting includes a parallelepiped housing with a plurality of air vents disposed diagonally across a front and a back surface. These air vents ensure the scent is dispersed into the ambient surroundings, and into the concurrent airflow, when the device is used.

The air freshener cartridge with mounting also includes a disposable air freshener cartridge. This cartridge is removably insertable into the housing, and releasably secured therein by means of a pair of triangular catches, said catches disposed protruding outward from a left and right side of a cartridge perimeter frame. These catches releasably engage with a pair of triangular nooks disposed in a left and right side of the housing.

It is envisioned that the disposable cartridge will have a specific scent, and that other disposable cartridges of a particular scent will be available for purchase and use with the device, each of the disposable cartridges releasably insertable into the housing.

The present device, therefore, is installable upon an extant air vent cover to disperse scent, as desired, throughout a building in which said air vent is located, the scent dispelled through the duct work connected to said vent to be distributed with the climate controlled airflow as part of a building's heating and cooling system. The present device, therefore, offers an efficient and simple method for controlling odors within a building. Replacing the disposable cartridge will ensure a ready supply of a desired scent is evenly distributed throughout the building, and individual cartridges may be changed to alter scent as desired thus enabling themed olfactory experiences for people moving through said building, as desired.

Thus has been broadly outlined the more important features of the present air freshener cartridge with mounting so that the detailed description thereof that follows may be better understood and in order that the present contribution to the art may be better appreciated.

Objects of the present air freshener cartridge with mounting, along with various novel features that characterize the invention are particularly pointed out in the claims forming a part of this disclosure. For better understanding of the air freshener cartridge with mounting, its operating advantages and specific objects attained by its uses, refer to the accompanying drawings and description.

BRIEF DESCRIPTION OF THE DRAWINGS FIGURES

Figure 4:
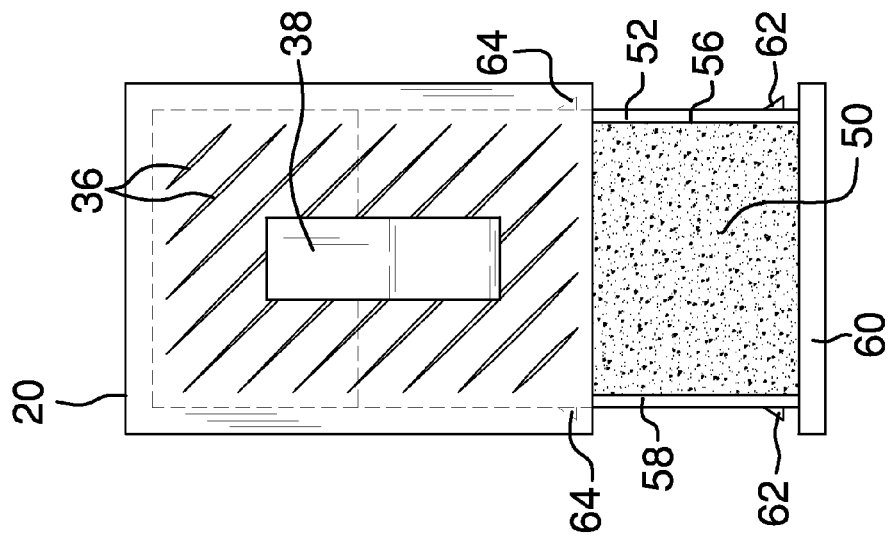
Figure 3:
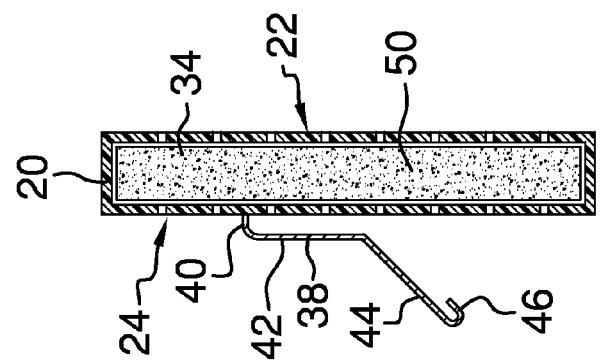
Figure 2:
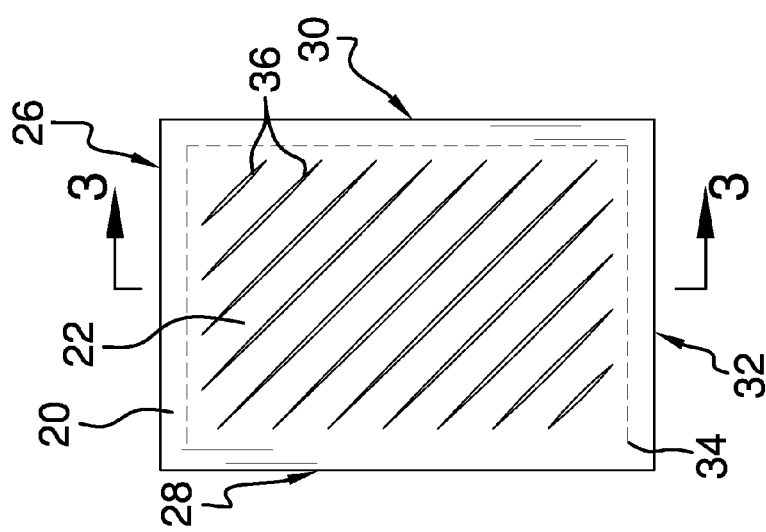
Figure 5:
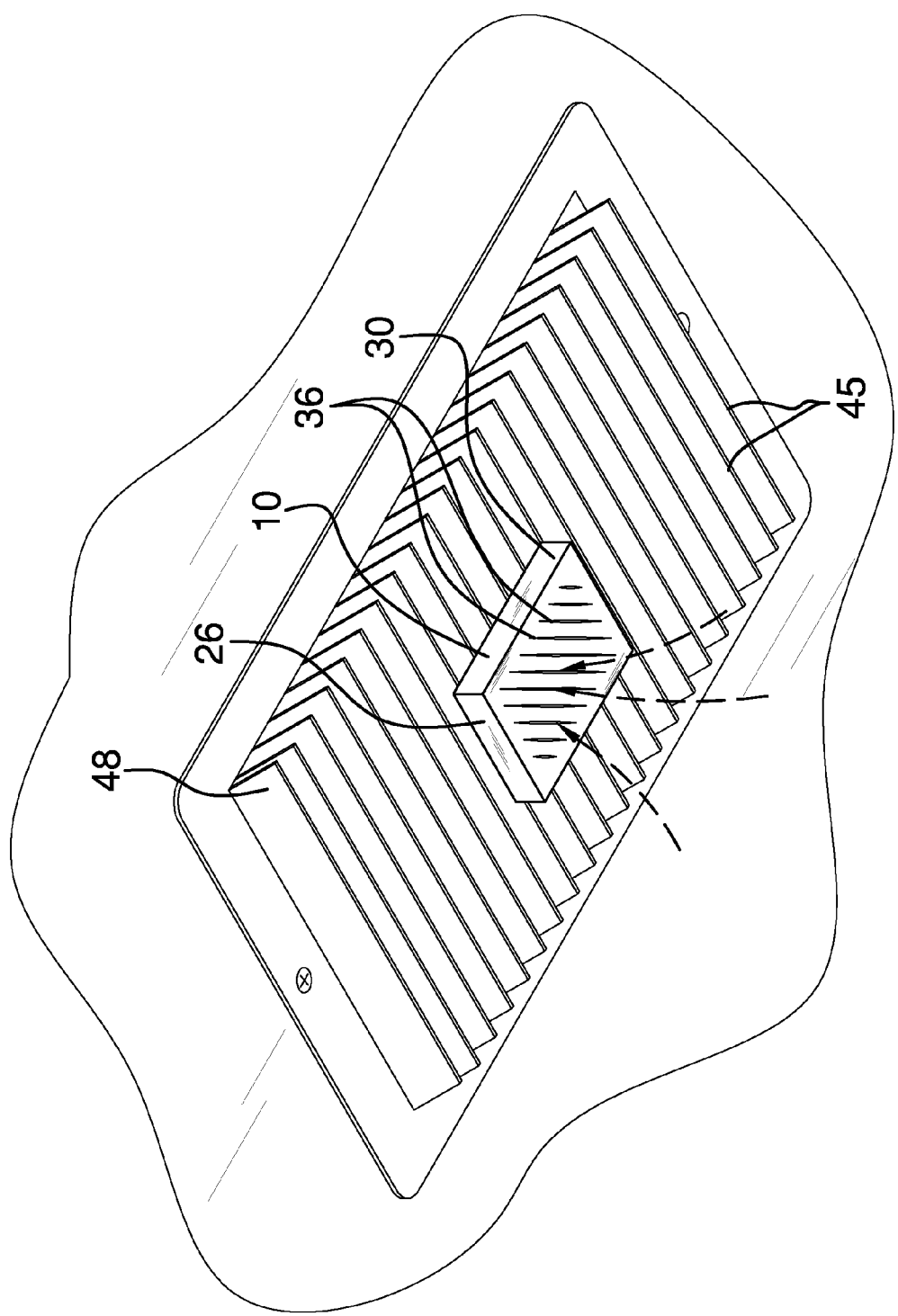

FIG. 1 is a back isometric view.
FIG. 2 is a front view.
FIG. 3 is a cross section view taken along the line 3-3 of FIG. 2.
FIG. 4 is a rear view illustrating a cartridge insertion into a housing.
FIG. 5 is an in use view.
FIG. 6 is a side view detailing the attachment of the device to an air vent cover.

DETAILED DESCRIPTION OF THE DRAWINGS

With reference now to the drawings, and in particular FIGS. 1 through 6 thereof, example of the instant air freshener cartridge with mounting employing the principles and concepts of the present air freshener cartridge with mounting and generally designated by the reference number 10 will be described.

Referring to FIGS. 1 through 6 a preferred embodiment of the present air freshener cartridge with mounting 10 is illustrated.

The air freshener cartridge with mounting 10 includes a polymeric parallelepiped housing 20. The housing 20 includes a front surface 22, a back surface 24, a top side 26, a left side 28, a right side 30, an open bottom 32, and a central cavity 34 accessible through the open bottom 32.

A plurality of air vents 36 is disposed across the front surface 22 and the back surface 24. In the preferred embodiment illustrated in this specification, the plurality of air vents 36 are disposed diagonally as a series of slots across the front 22 and back 24 surfaces.

A mounting clip 38 is disposed on the back surface 24, the mounting clip 38 includes a curved top section 40 connected to the housing 20. A vertical portion 42 is connected to the top section 40, the vertical portion 42 is disposed parallel the back surface 24. An attachment portion 44 is connected to the vertical portion 42, the attachment portion 44 is disposed approximately forty-five degrees with respect to the vertical section 42. A second curved section 46 connected to the attachment portion 44, the second curved section 46 configured to releasably engage an air vent cover 48. The mounting clip 38 releasably engages with an extant air vent cover 48 to secure the housing 20 normal with respect to the direction of airflow.

A parallelepiped air freshener cartridge 50 is removably insertable into the housing 20. The air freshener cartridge 50 includes a perimeter frame 52 with a top side 54, a first side 56 and a second side 58. A base plate 60 is attached to the first 56 and second 58 sides, the base plate 60 disposed parallel the top side. Each of a pair of catches 62 is disposed outwardly on the first side 56 and the second side 58. The pair of catches 62 releasably secure the cartridge 50 inside the housing 20, each of the pair of catches 62 is a triangle protrusion disposed proximal to the base plate 60 outfacing from the first 56 and second 58 sides of the perimeter frame 52, each of said catches 62 releasably engaging with each of a pair of triangular nooks 64 disposed in the housing 20 cavity 34, in the left 28 and the right 30 sides.

This air freshener cartridge 50 is replaceable, the housing 20 releasably receiving prefabricated cartridges 50, as desired. Each replaceable cartridge 50 is envisioned to be available with a specific scent.

What is claimed is:

1. An air freshener cartridge with mounting comprising:
   a polymeric parallelepiped housing comprising:
   a front surface;
   a back surface;
   a top side;
   a left side;
   a right side;
   an open bottom;
   a central cavity accessible through the open bottom;
   a plurality of air vents disposed across the front surface and the back surface;
   a mounting clip disposed on the back surface, the mounting clip comprising:
   a curved top section connected to the housing;
   a vertical portion connected to the top section, the vertical portion disposed parallel the back surface;
   an attachment portion connected to the vertical portion, the attachment portion disposed approximately forty-five degrees with respect to the vertical portion;
   a second curved section connected to the attachment portion, the second curved section configured to releasably engage an air vent cover;
   a parallelepiped air freshener cartridge comprising:
   a perimeter frame with a top side, a first side, and a second side;
   a base plate attached to the first and second sides, the base plate disposed parallel the top side;
   a pair of catches, each of the par of catches disposed outwardly on the first side and the second side;
   wherein the air freshener cartridge is removably insertable into the housing, the pair of catches releasably securing said cartridge inside the housing, whereby the mounting clip releasably engages with an extant air vent cover to secure the housing normal with respect to the direction of airflow.

2. The air freshener cartridge with mounting of claim 1 wherein the plurality of air vents are disposed diagonally across the front and back surfaces.

3. The air freshener cartridge with mounting of claim 2 wherein the air freshener cartridge is replaceable, the housing releasably receiving prefabricated cartridges, as desired.

4. The air freshener cartridge with mounting of claim 3 wherein each replaceable cartridge is available with a specific scent.

5. The air freshener cartridge with mounting of claim 4 wherein each of the pair of catches is a triangle protrusion disposed proximal to the base plate outfacing from the first and second sides of the perimeter frame, each of said catches releasably engaging with each of a pair of triangular nooks disposed in the housing cavity, in the left and the right sides.

* * * * *